US010492929B2

United States Patent
Termanini et al.

(10) Patent No.: US 10,492,929 B2
(45) Date of Patent: Dec. 3, 2019

(54) TOOL AND METHOD FOR SEPARATING A FEMORAL CUP OR A FEMORAL BALL FROM A FEMORAL IMPLANT

(71) Applicant: HIP INNOVATION TECHNOLOGY, LLC., Plantation, FL (US)

(72) Inventors: Zafer Termanini, Port Saint Lucie, FL (US); Brian VanHiel, Smyrna, GA (US); Kirk Charles, Austell, GA (US); Taylor Davis, Atlanta, GA (US)

(73) Assignee: JOINT INNOVATION TECHNOLOGY, LLC, Boca Raton, FL (US)

( * ) Notice: Subject to any disclaimer, the term of this patent is extended or adjusted under 35 U.S.C. 154(b) by 0 days.

(21) Appl. No.: 15/547,884

(22) PCT Filed: May 30, 2017

(86) PCT No.: PCT/US2017/034948
§ 371 (c)(1),
(2) Date: Aug. 1, 2017

(87) PCT Pub. No.: WO2018/026430
PCT Pub. Date: Feb. 8, 2018

(65) Prior Publication Data
US 2019/0142608 A1    May 16, 2019

Related U.S. Application Data

(60) Provisional application No. 62/369,901, filed on Aug. 2, 2016.

(51) Int. Cl.
*A61F 2/46* (2006.01)
*A61B 17/02* (2006.01)
(Continued)

(52) U.S. Cl.
CPC .......... *A61F 2/4637* (2013.01); *A61F 2/4607* (2013.01); *A61F 2002/30649* (2013.01);
(Continued)

(58) Field of Classification Search
CPC ........... A61B 17/025; A61B 2017/0275; A61F 2/4607; A61F 2/4609
See application file for complete search history.

(56) References Cited

U.S. PATENT DOCUMENTS

| 4,457,306 A | 7/1984 | Borzone |
| 4,898,161 A * | 2/1990 | Grundei ............... A61B 17/025 606/105 |

(Continued)

FOREIGN PATENT DOCUMENTS

WO       2017034846 A1    3/2017

OTHER PUBLICATIONS

International Search Report for corresponding application PCT/US2017/034948 dated Aug. 4, 2017.

*Primary Examiner* — Nicholas W Woodall
(74) *Attorney, Agent, or Firm* — Norris McLaughlin, PA (57) ABSTRACT

A surgical tool and method for separating a femoral cup or a femoral ball from an implanted femoral implant without disturbing the femoral implant. The tool is comprised of upper and lower lever arms which turn on an adjustable fulcrum. The upper lever arm has a distal end adapted to engage a femoral cup or a femoral ball and the distal end of the lower lever arm engages the implant. Proximal ends of the lever arms engage a drive assembly which is used to cause the distal ends to move away from one another thereby separating the femoral cup or ball from the femoral implant.

6 Claims, 13 Drawing Sheets

(51) Int. Cl.
*A61F 2/36* (2006.01)
*A61F 2/30* (2006.01)

(52) U.S. Cl.
CPC ............... *A61F 2002/3615* (2013.01); *A61F 2002/3654* (2013.01); *A61F 2002/4628* (2013.01); *A61F 2002/4641* (2013.01)

(56) References Cited

U.S. PATENT DOCUMENTS

| | | | |
|---|---|---|---|
| 7,377,182 B2 | 5/2008 | Serra et al. | |
| 8,393,254 B2 * | 3/2013 | Gao | A61B 17/2804 294/2 |
| 9,155,632 B2 | 10/2015 | Termanini | |
| 2005/0038441 A1 | 2/2005 | Hazebrouck | |
| 2018/0014823 A1 * | 1/2018 | Fahy | A01N 1/0247 |

* cited by examiner

TOOL AND METHOD FOR SEPARATING A FEMORAL CUP OR A FEMORAL BALL FROM A FEMORAL IMPLANT

This is an application filed under 35 USC 371 of PCT/US2017/34948 filed on 30 May 2017, which in turn claims priority to U.S. Ser. No. 62/369,901, filed 2 Aug. 2016. The enclosures of these foregoing applications is herein fully incorporated by reference. Further, the applicant claims the full priority benefit of these applications.

BACKGROUND OF THE INVENTION

Field of the Invention

The present invention relates to surgical instruments and methods used in connection with removing components of a reverse hip prosthesis or a conventional hip prosthesis from a patient. More particularly, the invention has to do with a surgical tool and method used in hip revision surgery to remove a femoral cup or a femoral ball from a femoral implant without loosening the femoral implant.

The Related Art

A reverse hip prosthesis is described in U.S. Pat. Nos. 8,313,531 B2 and 8,540,779 B2. The prosthesis and a revision surgery method also are described in U.S. Pat. No. 8,992,627 B2. The disclosures of these three patents are incorporated herein in their entireties by reference.

SUMMARY OF THE INVENTION

As described in the patents referenced above, the reverse hip prosthesis generally comprises an acetabular ball affixed to a stem in an acetabular cup and a femoral cup affixed to a femoral stem wherein the femoral cup articulates on the acetabular ball. In a conventional hip prosthesis an acetabular cup articulates on a femoral ball. The surgical tool and method of the invention enable a surgeon to separate the femoral cup or the femoral ball from a femoral implant in a patient in need of revision surgery. The femoral cup or femoral ball is affixed to the femoral implant by means of a Morse taper. The separation of the cup or ball from the implant requires releasing the bond with the implant which is achieved by means of the Morse taper. In the present disclosure we use the term "tools" from time to time to mean surgical tools.

DESCRIPTION OF THE PREFERRED EMBODIMENTS

Figure 1:
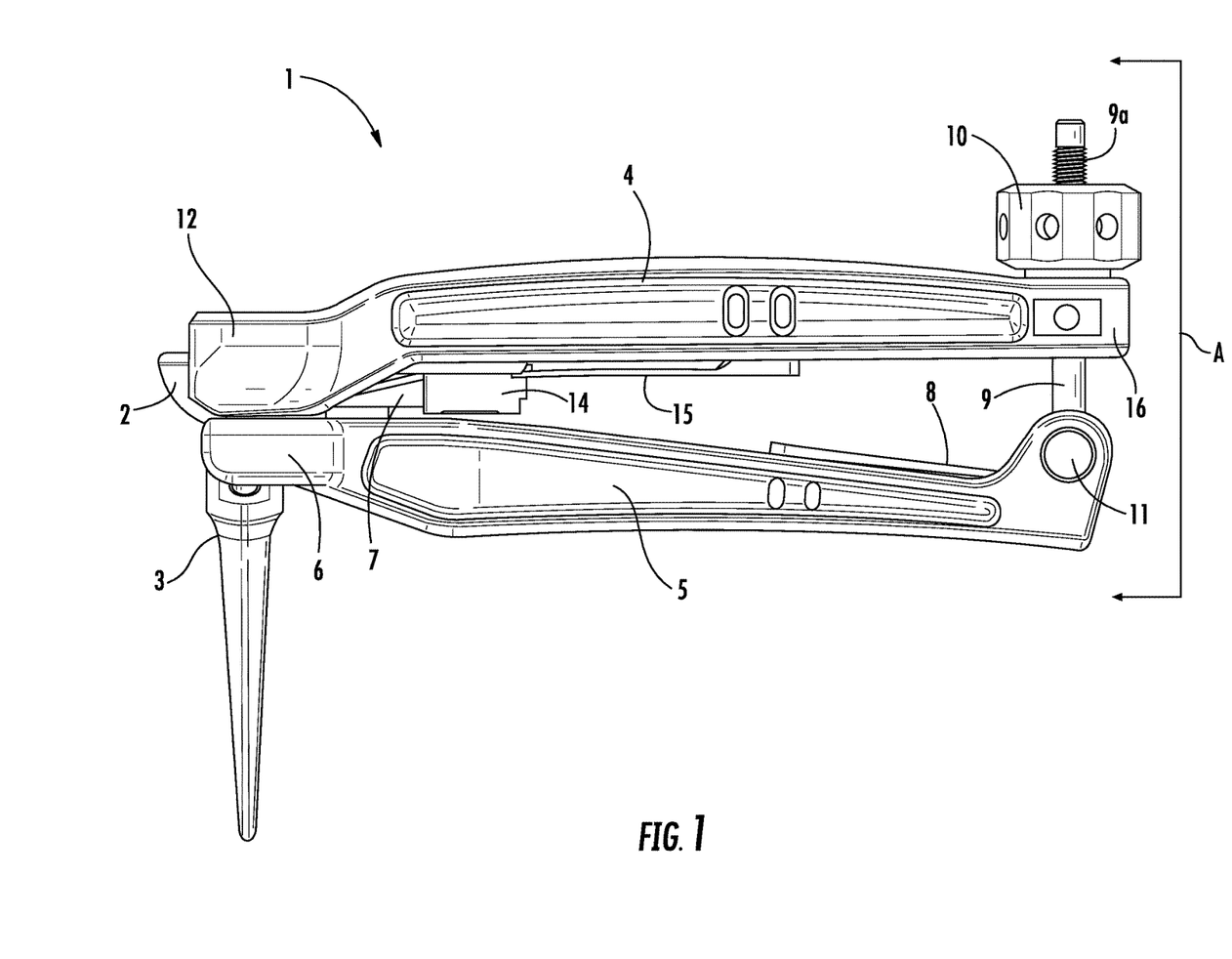
FIG. 1 is a side elevation view of a surgical tool of the invention engaged with a femoral cup and a femoral implant.
Figure 12:
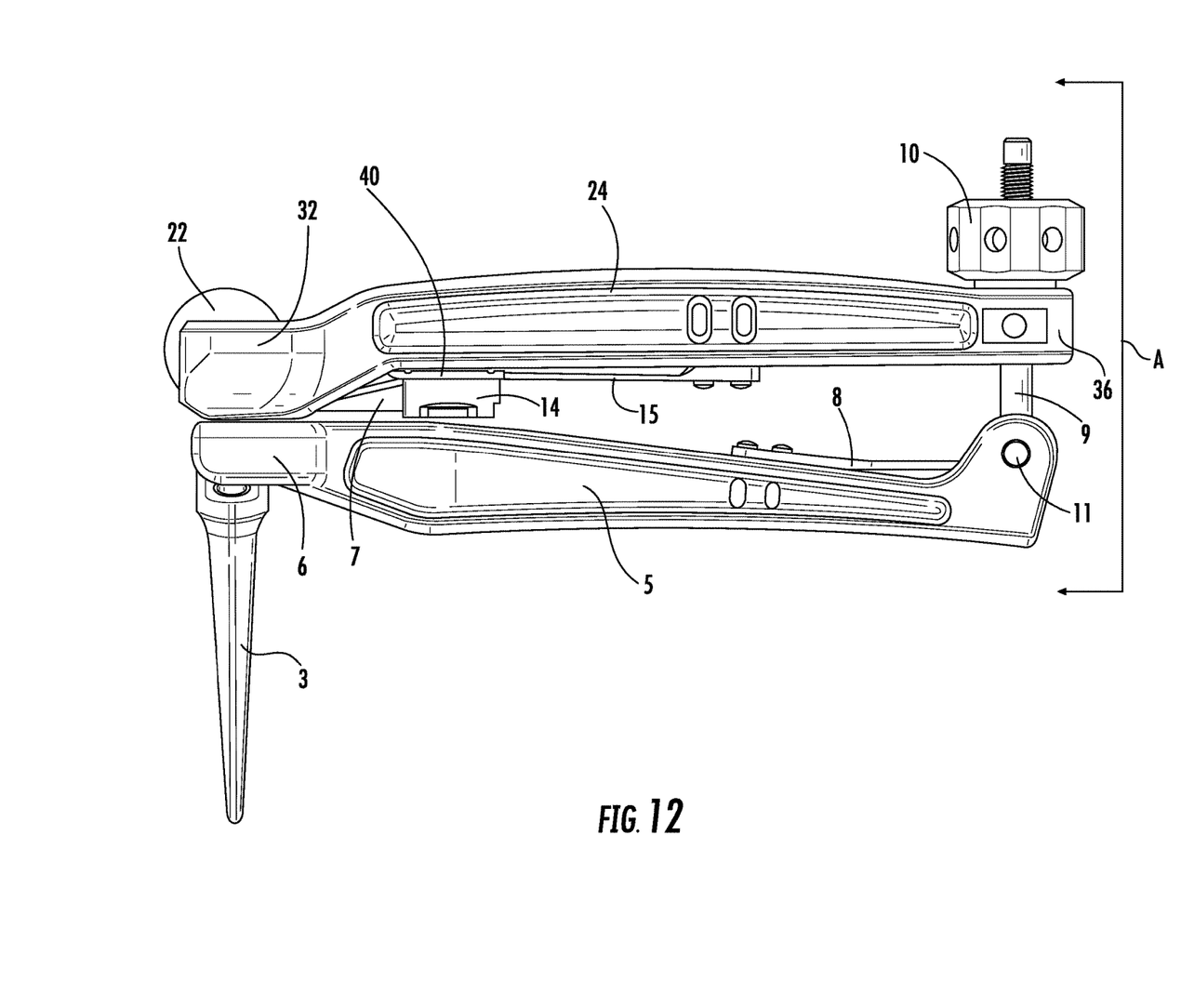
FIG. 12 is a side elevation view of the surgical tool of FIG. 10 engaged with a femoral ball and a femoral implant.
Figure 12A:
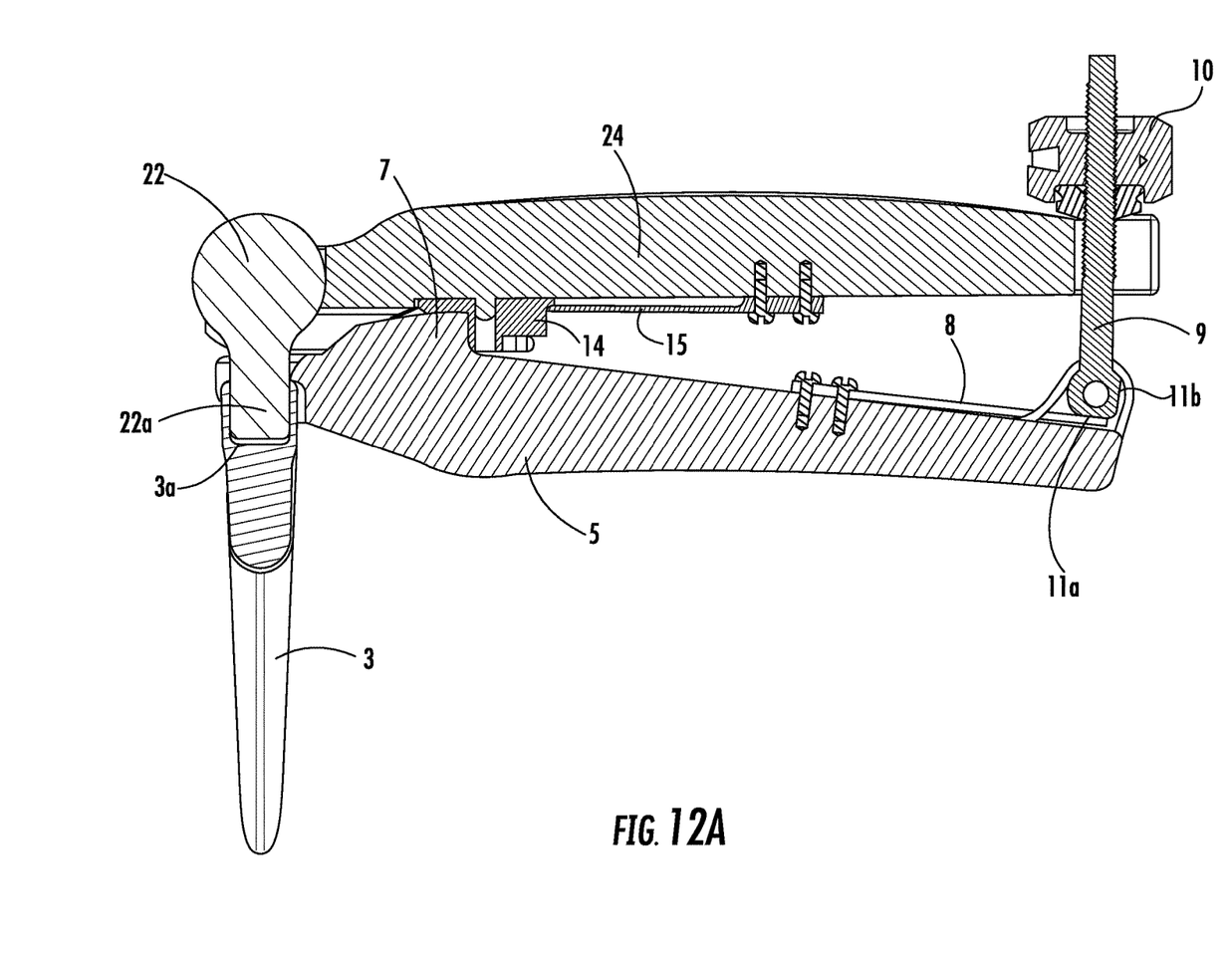
FIG. 12A is a section view of FIG. 12.

In FIG. 1, surgical tool 1 is engaged with femoral cup 2 and femoral implant 3. More specifically, the distal end of upper lever arm 4 is engaged with femoral cup 2 and the distal end of lower lever arm 5 is engaged with femoral implant 3. In a conventional hip prosthesis, a femoral ball 22 is affixed to femoral implant 3 in the same manner and position as femoral cup 2 is affixed to femoral implant 3. (See FIGS. 12 and 12A.) Femoral cup 2 has a neck 2a and femoral ball 22 has a neck 22a. The necks have a Morse taper and there is a Morse taper in socket 3a at the open proximal portion of implant 3.

Each lever arm comprises multiple components. Referring to FIGS. 1-8 and 8A, lower lever arm 5 comprises at its distal end an implant engagement fork 6, a fixed height adjustment ridge 7, an optional locking spring 8, and a pivotable drive assembly (described below). The implant engagement fork 6 is sized to engage the proximal end of an implanted femoral implant 3 and prevent the implant 3 from moving relative to a femoral bone when tool 1 is used to separate femoral cup 2 from implant 3. Fixed height adjustment ridge 7 works in cooperation with rotating turret 14 (see FIGS. 1-5, 9 and 9A) as discussed in detail below.

The pivotable drive assembly is comprised of a rod 9 having a threaded proximal portion 9a and a pivot pin 11 at its distal end. The central axis of rod 9 is perpendicular to the central axis of pin 11. Knob 10 is rotatably threaded onto rod 9 and is used to apply or release pressure on arm 4. When optional locking spring 8 is employed, the pivot pin 11 is provided with a flattened portion 11a which cooperates with spring 8 to maintain the drive assembly in engagement with upper lever arm 4 when desired. Flattened portion 11b of pivot pin 11 (see FIGS. 2 and 3) cooperates with spring 8 to maintain the drive assembly out of engagement with upper lever arm 4 when desired.

Optional locking spring 8 allows movement of the pivotable drive assembly into and out of engagement with the forked proximal end (drive assembly engagement fork 16) of upper lever arm 4. The spring helps to hold the assembly in or out of the engagement position as desired.

Referring to FIGS. 1-5, 9 and 9A, upper lever arm 4 comprises at its distal end femoral cup engagement fork 12. The bottom surface of lever arm 4 has a rotating turret 14 and a turret spring 15. At its proximal end, upper lever arm 4 is provided within drive assembly engagement fork 16.

The illustrated rotating turret 14 (see FIGS. 9A-D) is comprised of four flat portions, 14a-14d, but it is understood that it could be comprised of two or more flat portions, including more than the illustrated four flat portions. Spring 15 is biased against the cylindrical upper edge 40 (see FIGS. 3 and 9a) to allow the turret 14 to be rotated by hand while preventing it from rotating freely. Turret 14 rotates on pin 41 (see FIGS. 2 and 9B). Each flat portion 14a-14d is located in an indentation in turret 14 and each is in a plane in parallel with the plane of the bottom surface of lever arm 4 or 24. Said bottom surface is adjacent the cylindrical upper edge 40. The thickness of turret 14 at each flat portion is different such that the distance from the surface of each flat portion to the bottom surface or underside of the upper lever arm is different. Since the flat portions rest on ridge 7, the different thicknesses provide different distances of separation between the lever arms.

FIGS. 10-12A illustrate surgical tool 21, the embodiment of the invention which is used in revision surgery on a conventional hip prosthesis to remove a femoral ball from an implanted femoral implant. Comparing the tools of the invention, surgical tool 1 has an upper lever arm 4 with a femoral cup engagement fork 12 adapted to engage a femoral cup. And surgical tool 21 has an upper lever arm 24 with a femoral ball engagement fork 32 adapted to engage a femoral ball. Otherwise, the elements of surgical tool 21 are the same as those of surgical tool 1.

Referring to FIGS. 10-12A, all of the elements of lower lever arm 5 and the elements affixed thereto are the same as those of tool 1 and they function in the same way. Upper lever arm 24 comprises at its distal end a femoral ball engagement fork 32, rotating turret 14, turret spring 15 and, at its proximal end, drive assembly engagement fork 36.

The femoral cup or femoral ball engagement fork and the femoral implant engagement fork may be referred to generically herein as distal engagement forks.

The method of using the surgical tool 1 comprises engaging implant engagement fork 6 with neck 2a of femoral cup 2 and with the proximal end of implant 3. The fork 6 fits loosely around neck 2a, the neck serving to locate the fork 6 in position over the proximal end of femoral implant 3.

Then femoral cup engagement fork 12 is engaged with femoral cup 2 and rotating turret 14 is placed in contact with ridge 7. The appropriate position of rotating turret 14 is then determined and the turret is rotated to the optimum position as explained below.

Figure 2:
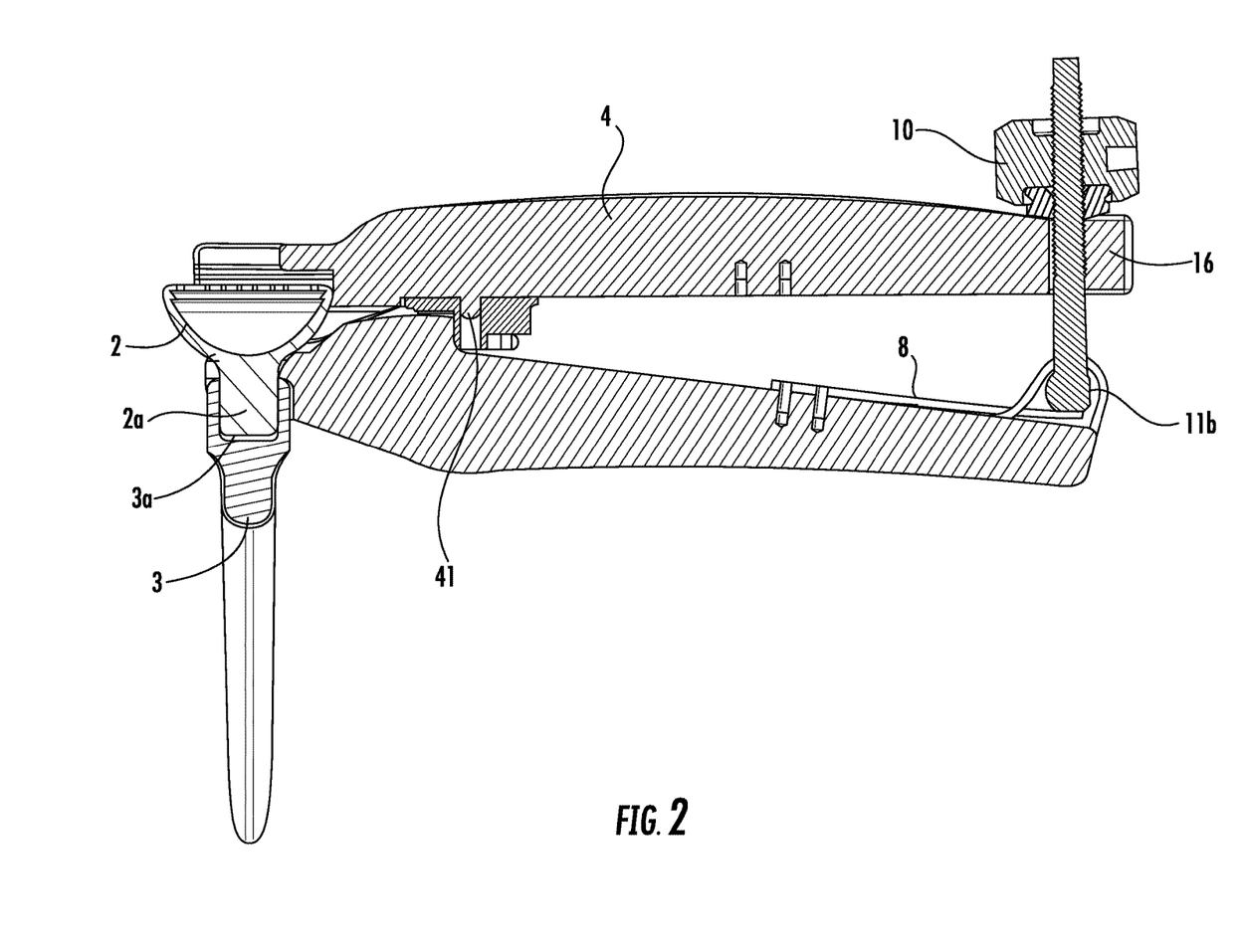
FIG. 2 is a section view of FIG. 1 taken along section lines A.
Figure 3:
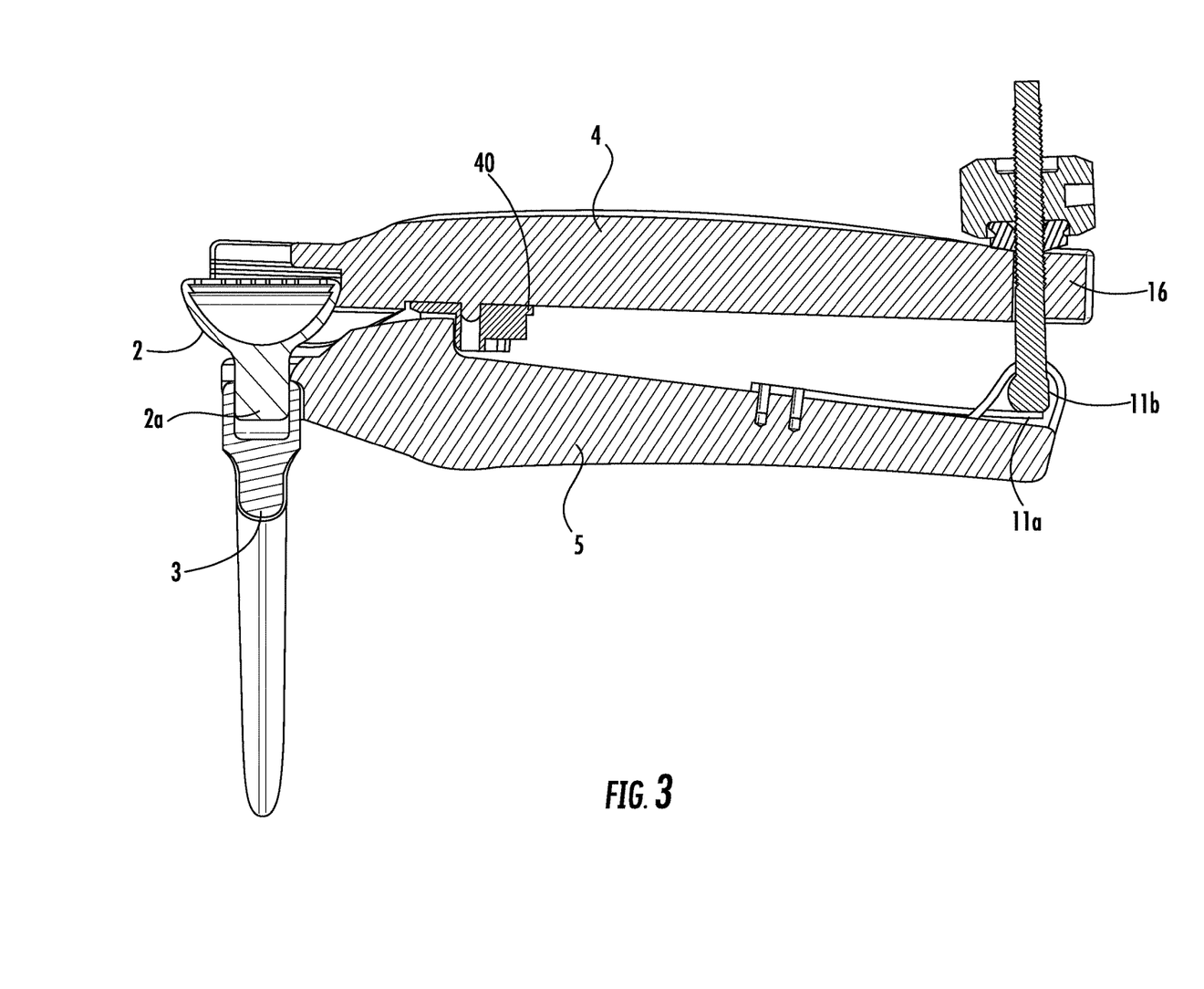
FIG. 3 is the same section as FIG. 2 after the femoral cup has been released from its Morse taper connection to the femoral implant.
Figure 4:
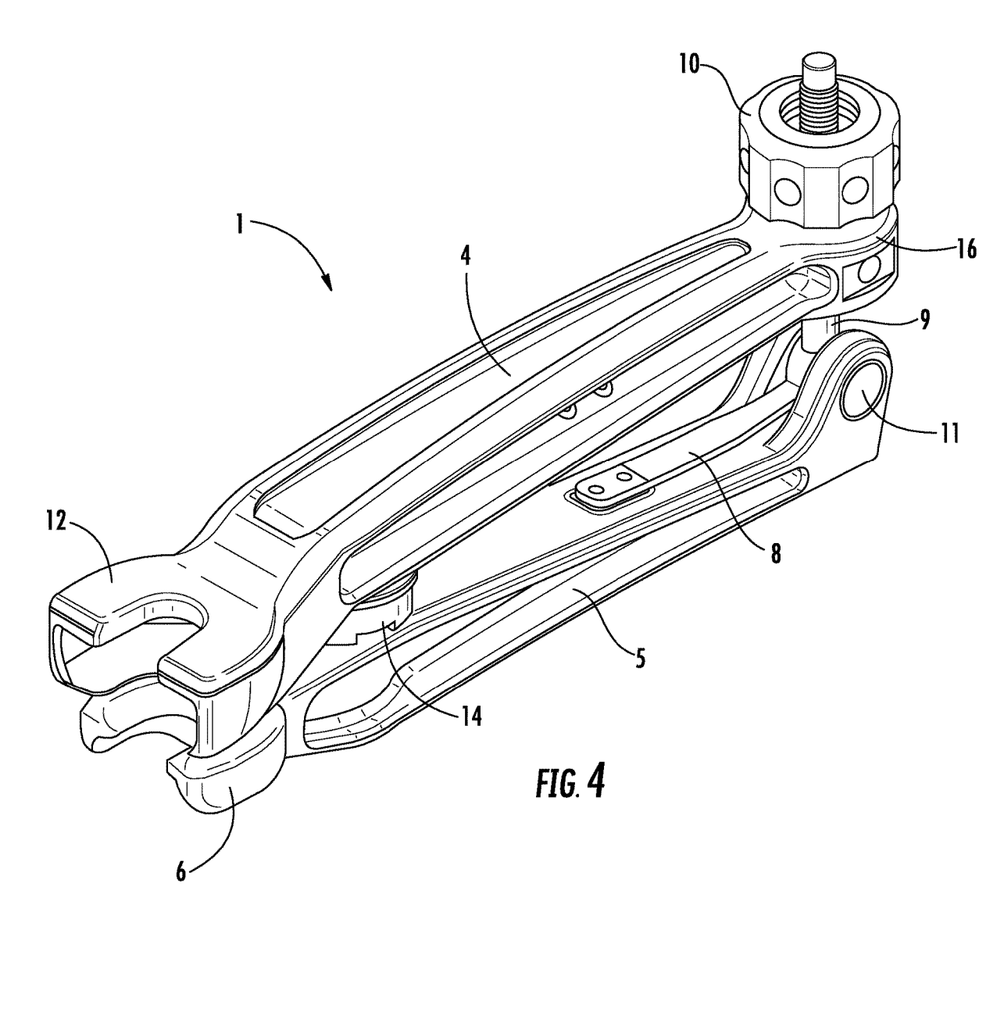
FIG. 4 is a perspective view of the surgical tool of FIG. 1.
Figure 5:
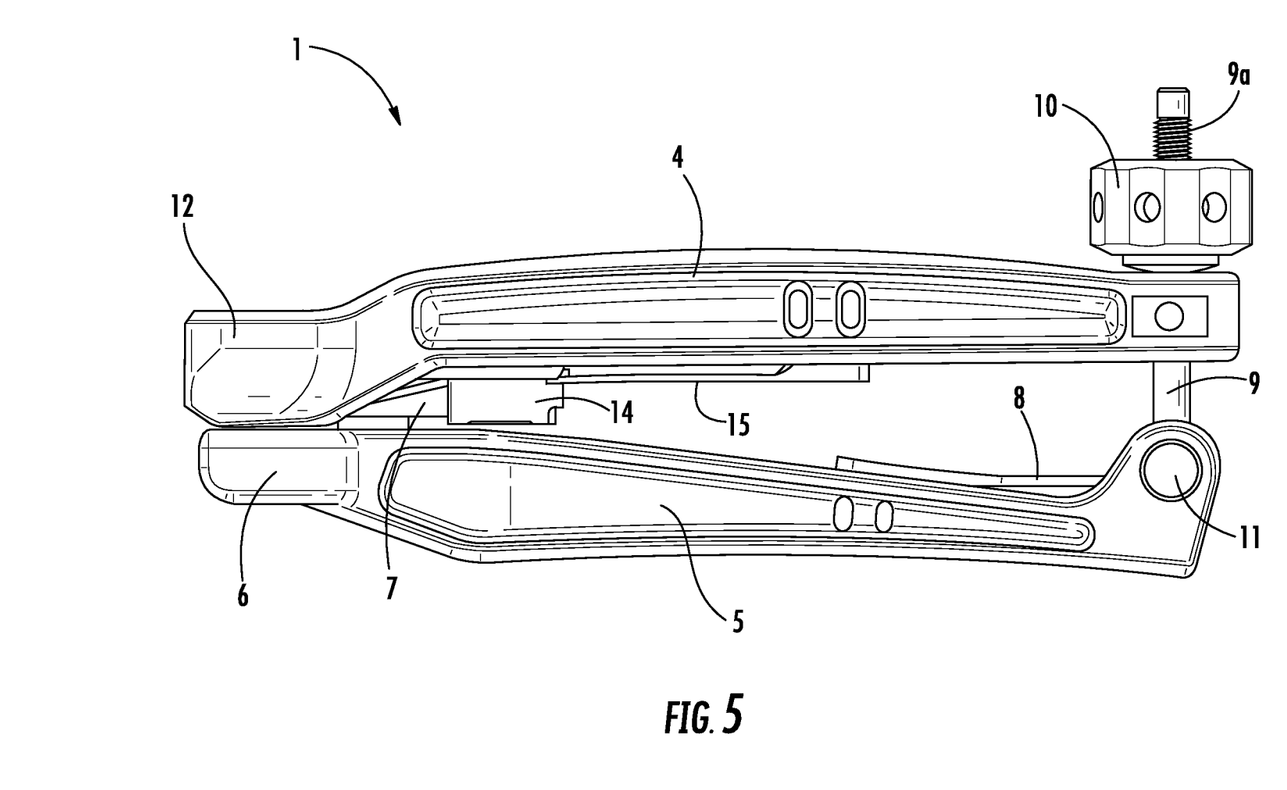
FIG. 5 is a side elevation view of the surgical tool of FIG. 1.
Figure 6:
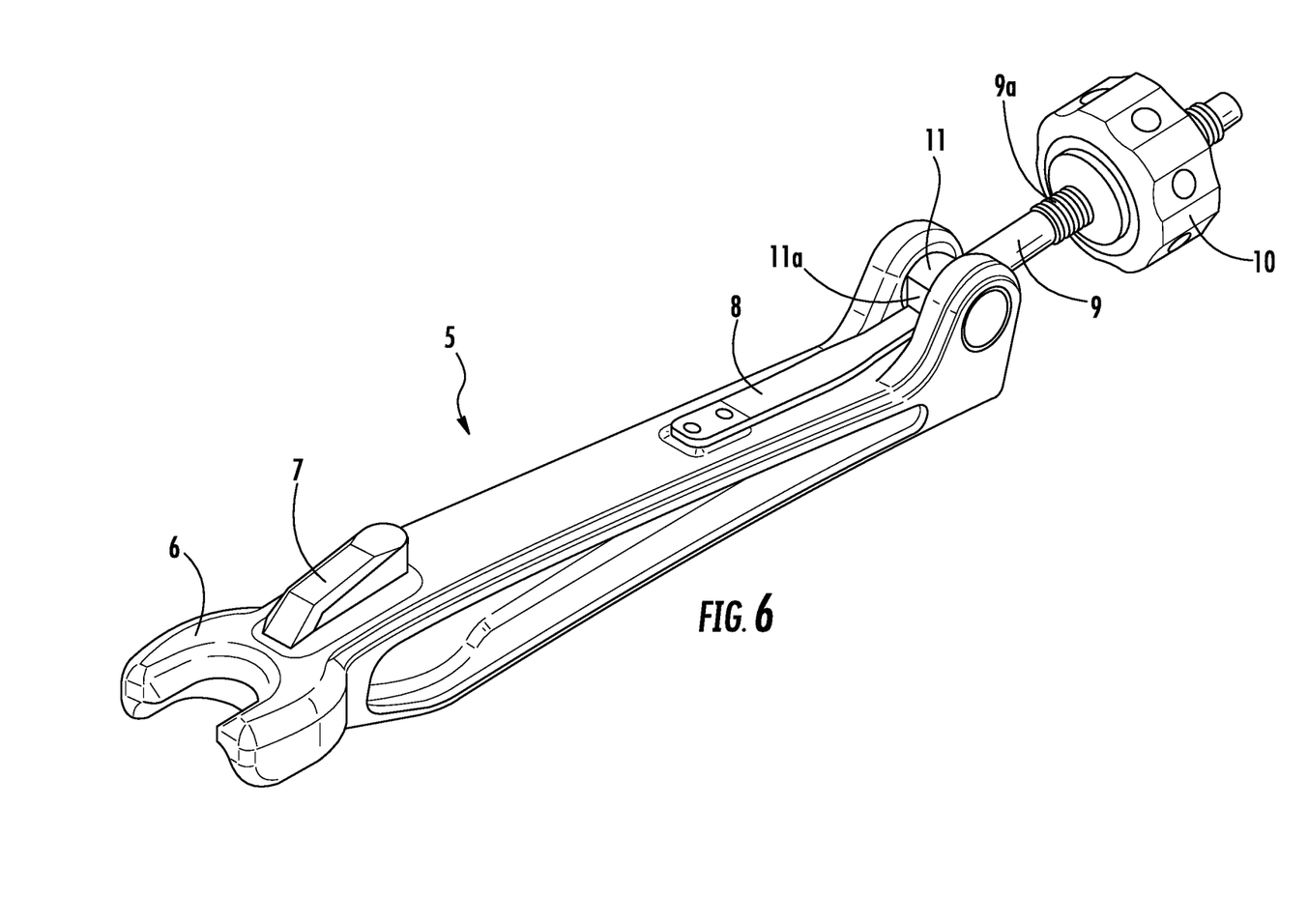
FIG. 6 is a perspective view of the lower lever arm of the surgical tool of FIG. 1.
Figure 7:
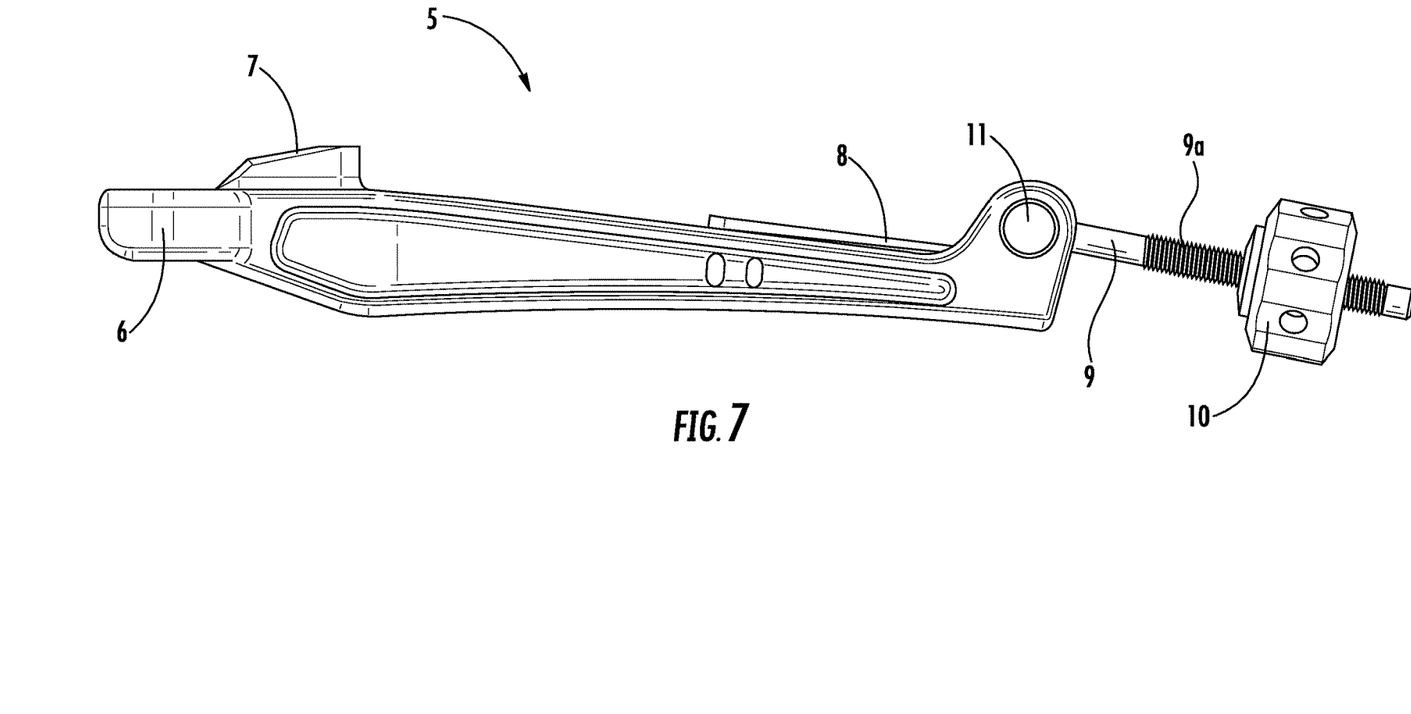
FIG. 7 is a side elevation view of the lower lever arm of the surgical tool of FIG. 1.
Figure 8:
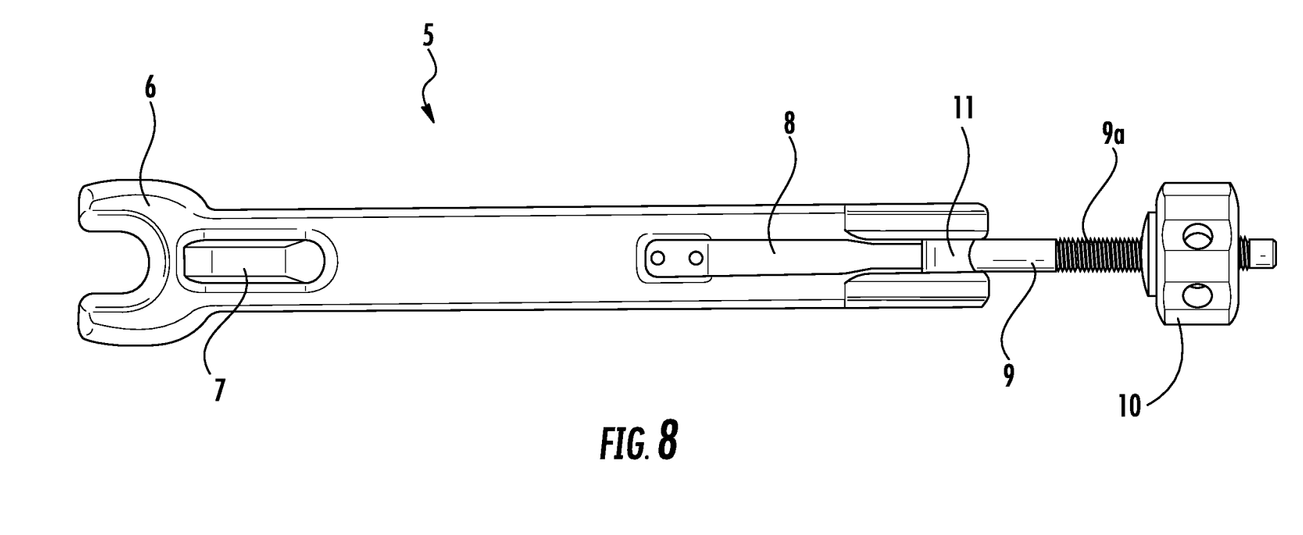
FIG. 8 is a top elevation view of the lower lever arm of the surgical tool of FIG. 1.
Figure 9A:
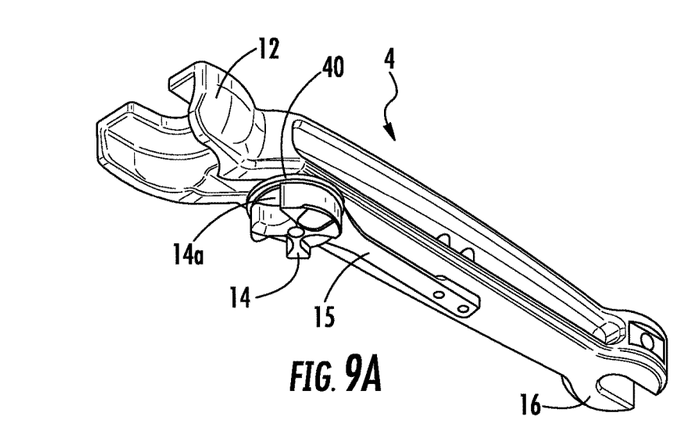
FIGS. 9A-9D are perspective views of the underside of the upper lever arm of the surgical tool of FIG. 1 illustrating the rotating turret in different positions of height adjustment, FIG. 9A illustrating the lower height, FIG. 9D illustrating the greatest height and FIGS. 9B and 9C illustrating intermediate heights.
Figures 9B, 9D:
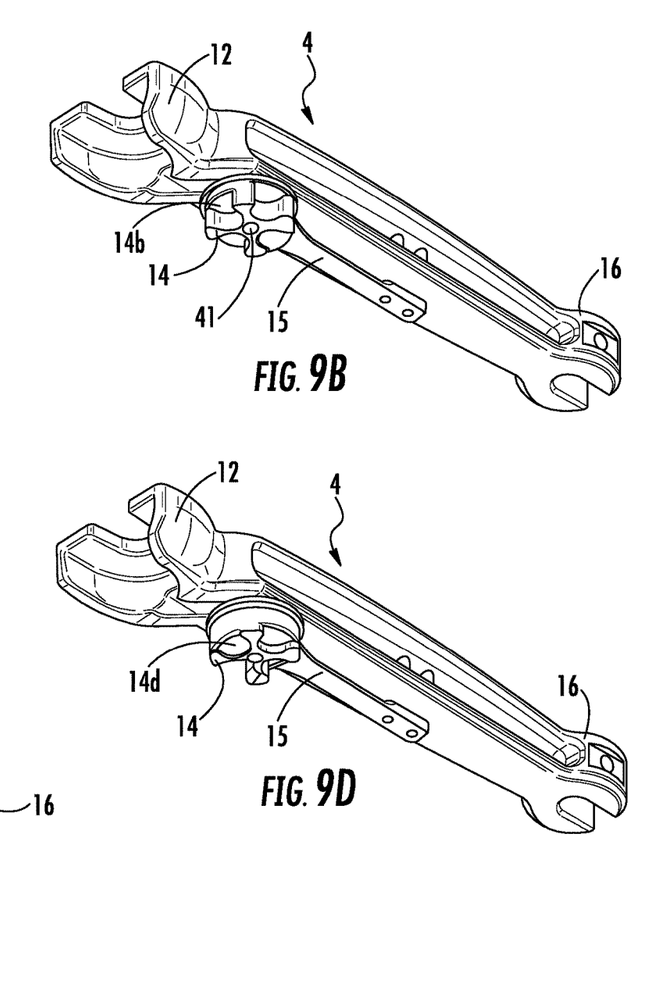
Figure 9C:
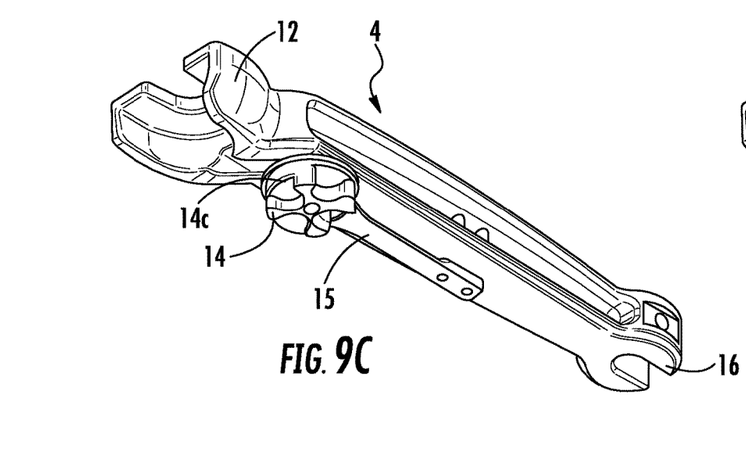
Figure 10:
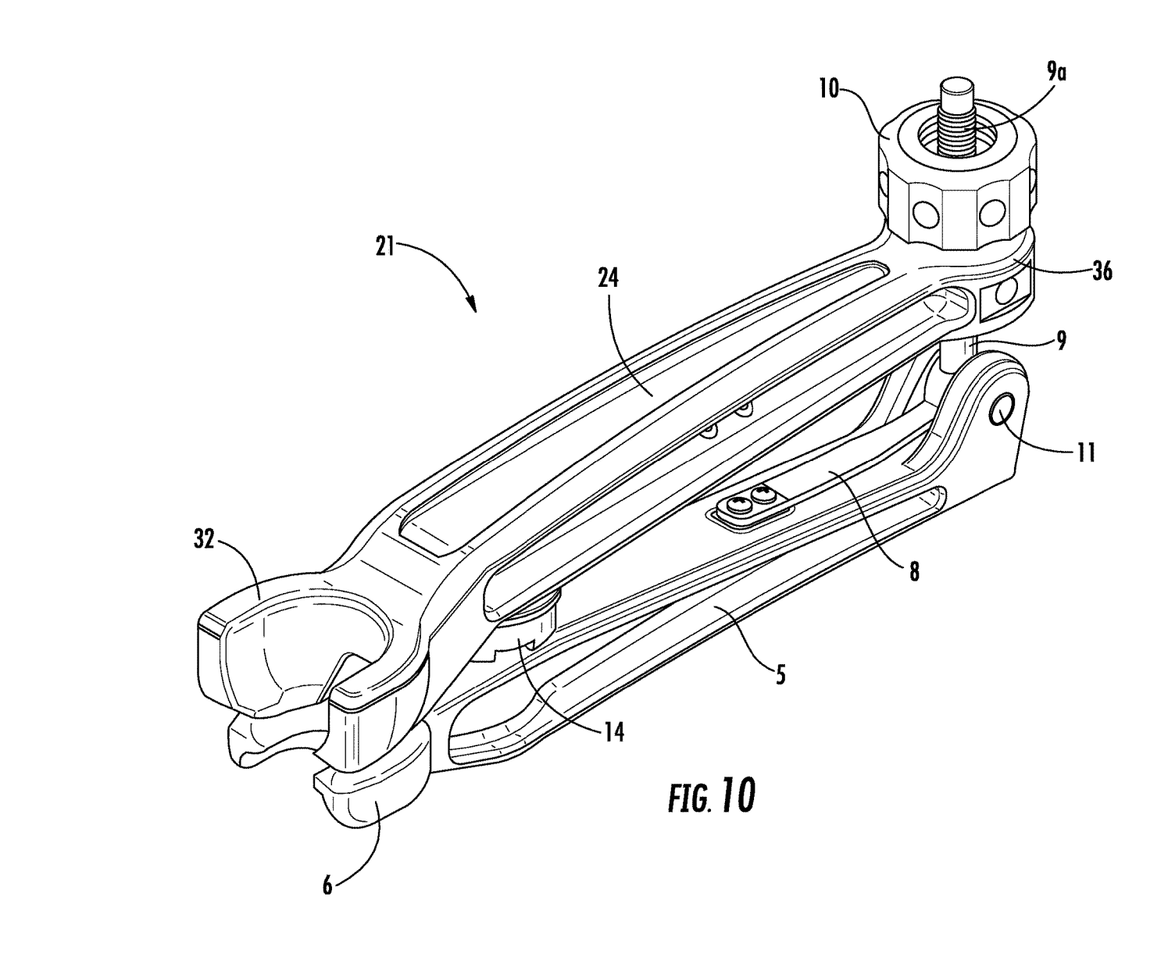
FIG. 10 is a perspective view of a surgical tool of the invention which is used to remove a femoral ball from a femoral implant.
Figure 11:
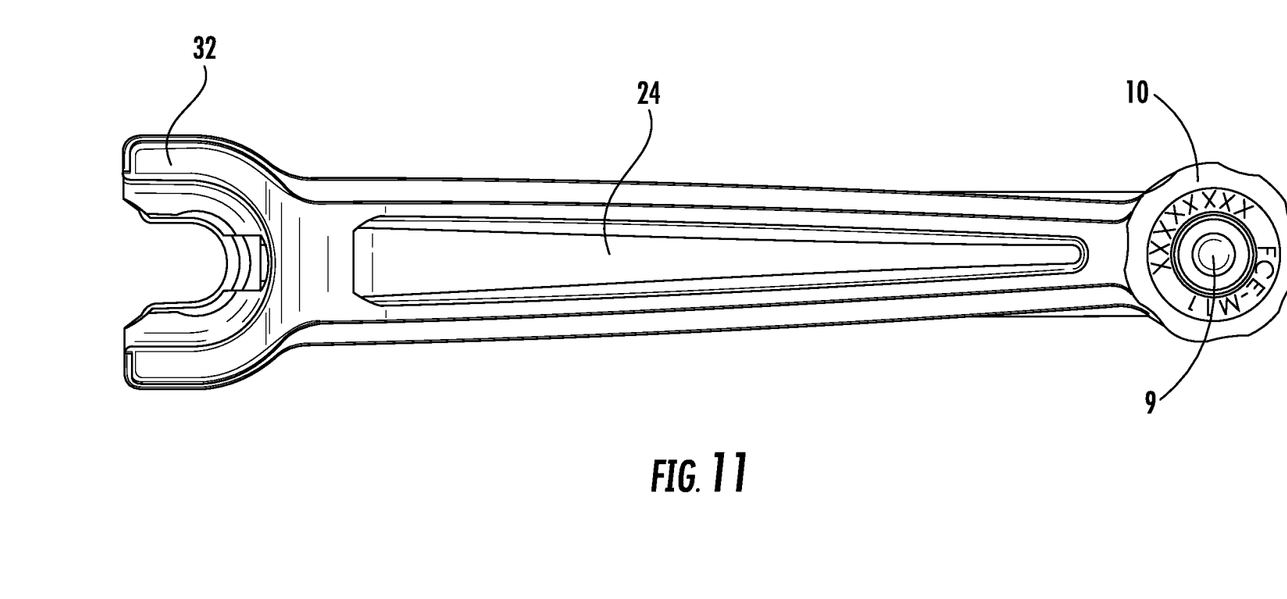
FIG. 11 is a top elevation view of FIG. 10.

When tool 1 is engaged with the femoral implant and the femoral cup, a flat portion, 14a, 14b, 14c or 14d, of turret 14 rests on ridge 7, the turret and the ridge providing a fulcrum for leverage in the operation of tool 1. Each flat portion provides a different distance of separation between the lever arms so that optimum leverage can be achieved depending upon the length of the neck extending beyond the proximal end of the femoral implant, as will be apparent to those having skill in the art. When the turret is rotated into the desired position, turret spring 15 serves to prevent the turret from rotating by itself. After the turret position is selected, the pivotable drive assembly is engaged with the drive assembly engagement fork 16 by pivoting the assembly into a position where rod 9 is brought within the fork 16 and knob 10 is backed off to a position above fork 16 as illustrated in FIGS. 1 and 2. Then knob 10 is tighteningly rotated to cause the proximal ends of levers 4 and 5 to move toward one another. This causes the distal ends of levers 4 and 5 to move away from one another, thereby causing the release of the cup from the femoral implant as illustrated in FIG. 3. This tightening rotation of knob 10 may be referred to herein as actuating the drive assembly.

The method and principles of using surgical tool 21 are the same as those described above in respect of tool 1. The only difference being that femoral ball engagement fork 32 is engaged with neck 22a of femoral ball 22.

A kit comprising both surgical tool 1 and surgical tool 21 may be made up of a lower lever arm 5 and its attendant components, an upper lever arm 4 and an upper lever arm 24 so that the kit may be used in revision surgery for a conventional hip prosthesis or a reverse hip prosthesis. The tools of the invention also may comprise an element or elements of a surgical kit which may contain other tools and/or implant elements.

We claim:

1. A surgical tool adapted to separate a femoral cup or a femoral ball from an implanted femoral implant comprising:
    an upper lever arm and a lower lever arm, the upper lever arm having an upper arm proximal end and an upper arm distal end and the lower lever arm having a lower lever arm proximal end and a lower lever arm distal end;
    a fulcrum comprised of a ridge disposed between the proximal and distal ends of the lever arms, the lever arms being in contact at the fulcrum;
    a femoral cup or femoral ball engagement fork disposed at the distal end of the upper lever arm;
    a femoral implant engagement fork disposed at the distal end of the lower lever arm;
    a rotating turret which cooperates with the ridge wherein rotation of the turret allows adjustment of the distance by which the lever arms may be separated;
    a drive assembly comprising a rod having a threaded proximal portion and a knob rotatably threaded thereon, the rod further comprising a pivot pin at its distal end pivotably attached to the proximal end of the lower lever arm, the upper lever arm having a drive assembly engagement fork at its proximal end, the drive assembly engagement fork being adapted to receive the rod disposed between the knob and the pivot pin; and
    the drive assembly being adapted to cause the proximal ends of the lever arms to move toward one another by means of rotation of the knob when the rod is disposed in the drive assembly engagement fork, thereby causing the distal ends of the lever arms to move away from one another as the lever arms turn on the fulcrum.

2. The surgical tool of claim 1, wherein the rotating turret has two or more flat portions in parallel with an underside of the upper lever arm, each flat portion being a different distance from said underside.

3. A method of using the tool of claim 1 to separate a femoral cup or a femoral ball from a femoral implant, the method comprising the steps of:
    engaging the femoral implant engagement fork with the femoral implant and engaging the femoral cup or femoral ball engagement fork with the femoral cup or the femoral ball and
    then causing the distal engagement forks to move away from one another by actuating the drive assembly.

4. The method according to claim 3, wherein the distance separating one lever arm from another is adjusted at the fulcrum by rotating the turret to thereby control the leverage imparted on the femoral cup or the femoral ball.

5. A kit comprising the surgical tool of claim 1, further which one or more other tools and/or implant elements.

6. A kit of claim 5, further comprising a femoral cup engagement fork and/or a femoral ball engagement fork.

* * * * *